US011288445B2

(12) United States Patent
Burns et al.

(10) Patent No.: US 11,288,445 B2
(45) Date of Patent: Mar. 29, 2022

(54) AUTOMATED SYSTEM AND METHOD FOR ASSIGNING BILLING CODES TO MEDICAL PROCEDURES

(71) Applicant: THE REGENTS OF THE UNIVERSITY OF MICHIGAN, Ann Arbor, MI (US)

(72) Inventors: Michael L. Burns, Ann Arbor, MI (US); John Vandervest, Ann Arbor, MI (US); Sachin Kheterpal, Ann Arbor, MI (US); Nirav Jitendra Shah, Ann Arbor, MI (US); Leif Saager, Ann Arbor, MI (US); Jay Jeong, Ann Arbor, MI (US); Anik Sinha, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/709,069

(22) Filed: Dec. 10, 2019

(65) Prior Publication Data
US 2020/0226321 A1  Jul. 16, 2020

Related U.S. Application Data

(60) Provisional application No. 62/791,257, filed on Jan. 11, 2019.

(51) Int. Cl.
*G06F 40/174* (2020.01)
*G06N 20/20* (2019.01)
(Continued)

(52) U.S. Cl.
CPC .......... *G06F 40/174* (2020.01); *G06F 40/157* (2020.01); *G06N 20/20* (2019.01); *G16H 10/60* (2018.01)

(58) Field of Classification Search
CPC .... G06F 16/951; G06F 16/2228; G06F 16/33; G06F 16/345; G06F 16/35; G06F 16/355;
(Continued)

(56) References Cited

U.S. PATENT DOCUMENTS 5,325,293 A * 6/1994 Dome .................... G16H 70/20
705/2
6,915,254 B1 * 7/2005 Heinze .................... G06F 40/20
704/9

(Continued)

OTHER PUBLICATIONS

"Math Definitions", Published: Feb. 17, 2009, publisher: www.mathsisfun.com, pp. 1 (Year: 2009).*

*Primary Examiner* — Wilson W Tsui
(74) *Attorney, Agent, or Firm* — Harness, Dickey & Pierce, P.L.C.

(57) ABSTRACT

A method is presented for assigning billing codes for medical procedures. For each string in an input record describing a medical procedure in the input text description, comparing the string to entries in a dictionary of common misspelling and, in response to the string matching an entry in the dictionary, replacing the string with proper spelling; for each string in the input record, comparing the string to entries in another dictionary of abbreviations and, in response to the string matching an entry in the dictionary, replacing the string with expanded text for the abbreviation; constructing a feature vector by extracting features from the input record; for each billing code in a listing of possible billing codes, computing a classifier score for the feature vector using machine learning; and assigning a billing code to the input record from the listing of possible billing codes based on the classifier scores.

7 Claims, 6 Drawing Sheets

(51) Int. Cl.
*G06F 40/157* (2020.01)
*G16H 10/60* (2018.01)

(58) Field of Classification Search
CPC ...... G06F 40/10; G06F 40/205; G06F 40/174;
G06F 40/157; G16H 10/60; G06N 20/20
See application file for complete search history.

(56) References Cited

U.S. PATENT DOCUMENTS

| | | | |
|---|---|---|---|
| 7,574,369 B1 | 8/2009 | Borza | |
| 7,610,192 B1* | 10/2009 | Jamieson | G06Q 40/08 704/9 |
| 9,124,776 B2 | 9/2015 | Woo | |
| 2002/0120466 A1 | 8/2002 | Finn | |
| 2003/0208379 A1* | 11/2003 | Haskey | G06Q 40/08 705/2 |
| 2004/0117206 A1* | 6/2004 | Steinberger | G16H 70/20 705/2 |
| 2004/0172297 A1* | 9/2004 | Rao | G06Q 10/10 705/2 |
| 2005/0033612 A1 | 2/2005 | Donovan et al. | |
| 2005/0149358 A1 | 7/2005 | Sacco et al. | |
| 2007/0005597 A1* | 1/2007 | Williams | G06F 16/33 |
| 2011/0040576 A1* | 2/2011 | Madan | G16H 10/60 705/3 |
| 2011/0295612 A1* | 12/2011 | Donneau-Golencer | G06Q 30/02 705/1.1 |
| 2014/0379718 A1* | 12/2014 | Halter | G06F 16/35 707/738 |
| 2015/0039339 A1 | 2/2015 | Ellington et al. | |
| 2015/0294338 A1 | 10/2015 | Ketchel, III et al. | |
| 2015/0356647 A1* | 12/2015 | Reiser | G06Q 10/10 705/3 |
| 2016/0203287 A1* | 7/2016 | Chen | G16H 50/70 705/3 |
| 2017/0337334 A1* | 11/2017 | Stanczak | G06Q 30/04 |

\* cited by examiner

|  | 01173 | 01112 | 01120 | 01170 | 01160 | 01130 |
|---|---|---|---|---|---|---|
| 00670 | 0.0 | 0.0 | 0.0 | 3.5 | 1.6 | 0.0 |
| 01922 | 0.0 | 2.0 | 1.0 | 0.0 | 0.0 | 0.0 |
| 01250 | 0.0 | 0.0 | 1.6 | 0.0 | 0.0 | 0.0 |
| 01210 | 0.0 | 1.6 | 3.5 | 3.0 | 0.0 | 0.0 |
| 00910 | 1.0 | 1.6 | 0.0 | 0.0 | 0.0 | 0.0 |
| 00532 | 0.0 | 3.5 | 0.0 | 0.0 | 0.0 | 0.0 |
| 01928 | 0.0 | 0.0 | 0.0 | 1.0 | 0.0 | 0.0 |
| 00300 | 0.0 | 0.0 | 3.6 | 0.0 | 0.0 | 0.0 |
| 00902 | 0.0 | 0.0 | 2.0 | 0.0 | 0.0 | 0.0 |
| 01464 | 0.0 | 1.6 | 0.0 | 0.0 | 0.0 | 0.0 |
| 00635 | 0.0 | 2.3 | 0.0 | 0.0 | 0.0 | 0.0 |
| 01484 | 0.0 | 1.0 | 0.0 | 0.0 | 0.0 | 0.0 |
| 01952 | 0.0 | 0.0 | 1.0 | 0.0 | 0.0 | 0.0 |
| 00214 | 0.0 | 0.0 | 0.0 | 1.0 | 0.0 | 0.0 |
| 00400 | 1.0 | 0.0 | 3.8 | 1.0 | 2.0 | 0.0 |
| 01480 | 2.0 | 4.5 | 3.7 | 2.0 | 0.0 | 0.0 |
| 01215 | 0.0 | 0.0 | 1.0 | 0.0 | 0.0 | 0.0 |
| 01130 | 0.0 | 0.0 | 0.0 | 0.0 | 0.0 | 5.4 |
| 01160 | 1.6 | 1.0 | 1.6 | 1.6 | 2.6 | 0.0 |
| 01170 | 2.6 | 0.0 | 2.6 | 5.2 | 4.0 | 0.0 |
| 01120 | 1.6 | 0.0 | 5.5 | 2.3 | 0.0 | 0.0 |
| 01112 | 0.0 | 8.9 | 1.6 | 0.0 | 0.0 | 0.0 |
| 01173 | 6.6 | 0.0 | 2.6 | 3.6 | 1.6 | 0.0 |

FIG. 5

AUTOMATED SYSTEM AND METHOD FOR ASSIGNING BILLING CODES TO MEDICAL PROCEDURES

CROSS-REFERENCE TO RELATED APPLICATIONS

This application claims the benefit of U.S. Provisional Application No. 62/791,257 filed on Jan. 11, 2019. The entire disclosure of the above application is incorporated herein by reference.

FIELD

The present disclosure relates to an automated system and methods for assigning billing codes to medical procedures.

BACKGROUND

Accurate billing and coding is essential to the viability of anesthesiology practices. Anesthesiology billing data is additionally used in quality and research projects. At the Multicenter Perioperative Group (MPOG), registry billing data is critical for case categorization and timely provider feedback. However, as billing is primarily a manual process there are frequently delays and billing data acquisition lags significantly behind clinical care.

Anesthesiology billing and reimbursement is a complex process that requires coordination and proper documentation from both administrative personnel and clinical providers. The majority of anesthesiology practices have specialized teams which process patient, administrative, and procedural information, translate this information into billing codes, and submit and handle reimbursements for the anesthesiology groups. These teams consist of professional billers and ancillary staff who streamline the task of billing assignment to minimize billing errors and time to reimbursement. Billing departments are an essential part of this process for most practices, but administrative costs in the United States are substantial, reaching 25.3% of US hospital expenditures with 18% representing billing and insurance-related activities and claims processing totaling billions of dollars in annual costs. The efficiencies of these departments is key to maintain financial viability and cost control.

Within the practice of Anesthesiology, professional billing staff are responsible for selecting Current Procedure Terminology (CPT) codes to describe anesthesia care provided within the case. These CPT codes are based on surgical procedures performed. The process of assigning CPT codes is complicated and labor-intensive requiring various resources including specialized trained coding personnel for Electronic Medical Record (EMR) extraction, transcription, translation, coding assignment, validation, and auditing. Despite this, error rates in medical coding can be high. Studies have shown high rates of error for standard CPT coding in anesthesia with specialized teams, with error rates as high as 38%. As an alternative, when physicians independently code CPTs for their procedures error rates can be even higher, 54% in one study of interventional radiologists. Furthermore, modest gains in efficiency of billing process can have large effects on revenue—one study showed that a decrease of 10.1 days in accounts receivable or a charge lag decrease of 7.3 days resulted in a revenue gain equivalent to 3.0% of total annual receipts in a single academic anesthesiology practice.

Therefore, it is desirable to develop an automated and accurate system and methods for assigning billing code to medical procedures. This section provides background information related to the present disclosure which is not necessarily prior art.

SUMMARY

This section provides a general summary of the disclosure, and is not a comprehensive disclosure of its full scope or all of its features.

A method is presented for assigning billing codes for medical procedures. In one aspect, the method includes: receiving a listing of possible billing codes, each billing code in the listing of possible billing codes includes a text description of a medical procedure associated with the billing code; receiving a first dictionary of common misspellings, each entry in the first dictionary includes a misspelled word and a corresponding proper spelling of the misspelled word; receiving a second dictionary of abbreviations, each entry in the second dictionary includes an abbreviation and expanded text for the abbreviation; receiving an input record describing a medical procedure, where the input record includes an input text description for the medical procedure; for each string in the input text description, comparing the string to entries in the first dictionary and, in response to the string matching a given entry in the first dictionary, replacing the string in the input text description with proper spelling; for each string in the input text description, comparing the string to entries in the second dictionary and, in response to the string matching a given entry in the second dictionary, replacing the string in the input text description with expanded text for the abbreviation; constructing, by the computer processor, a feature vector by extracting one or more features from the input record, where the input text description serves as a feature in the feature vector; for each billing code in the listing of possible billing codes, computing, by the computer processor, a classifier score for the feature vector using machine learning; and assigning a billing code to the input record from the listing of possible billing codes based on the classifier scores.

In another aspect, the method for assigning billing codes includes: receiving a listing of possible billing codes, each billing code in the listing of possible billing codes includes a text description of a medical procedure associated with the billing code; receiving an input record describing a medical procedure, where the input record includes an input text description for the medical procedure; constructing a feature vector by extracting one or more features from the input record, where the input text description serves as a feature in the feature vector; for each billing code in the listing of possible billing codes, computing a classifier score for the feature vector using machine learning; for each billing code in the listing of possible billing codes, computing a term frequency-inverse document frequency (Tf-IDF) score for the input text description in relation to the text description for a given billing code in the listing of possible billing codes, where the Tf-IDF score for the given billing code is a summation of each score for each string in the input text description; for each billing code in the listing of possible billing codes, combining the Tf-IDF score with the classifier score to form a composite score; and assigning a billing code to the input record from the listing of possible billing codes based on the composite scores for each of the billing codes in the listing of possible billing codes.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5 is a heat map for the Pelvic (except hip) CPT body area category using a Long Short-Term Memory (LSTM) machine learning algorithm. CPT codes on the left are the assignments from the institutional data while those along the bottom are chosen by the model. Numbers reflect the log 2(count+1), thus all values are in the range of 0-15 (count=0 to 2^15−1) such that the higher the value the larger the association.

Figure 6:
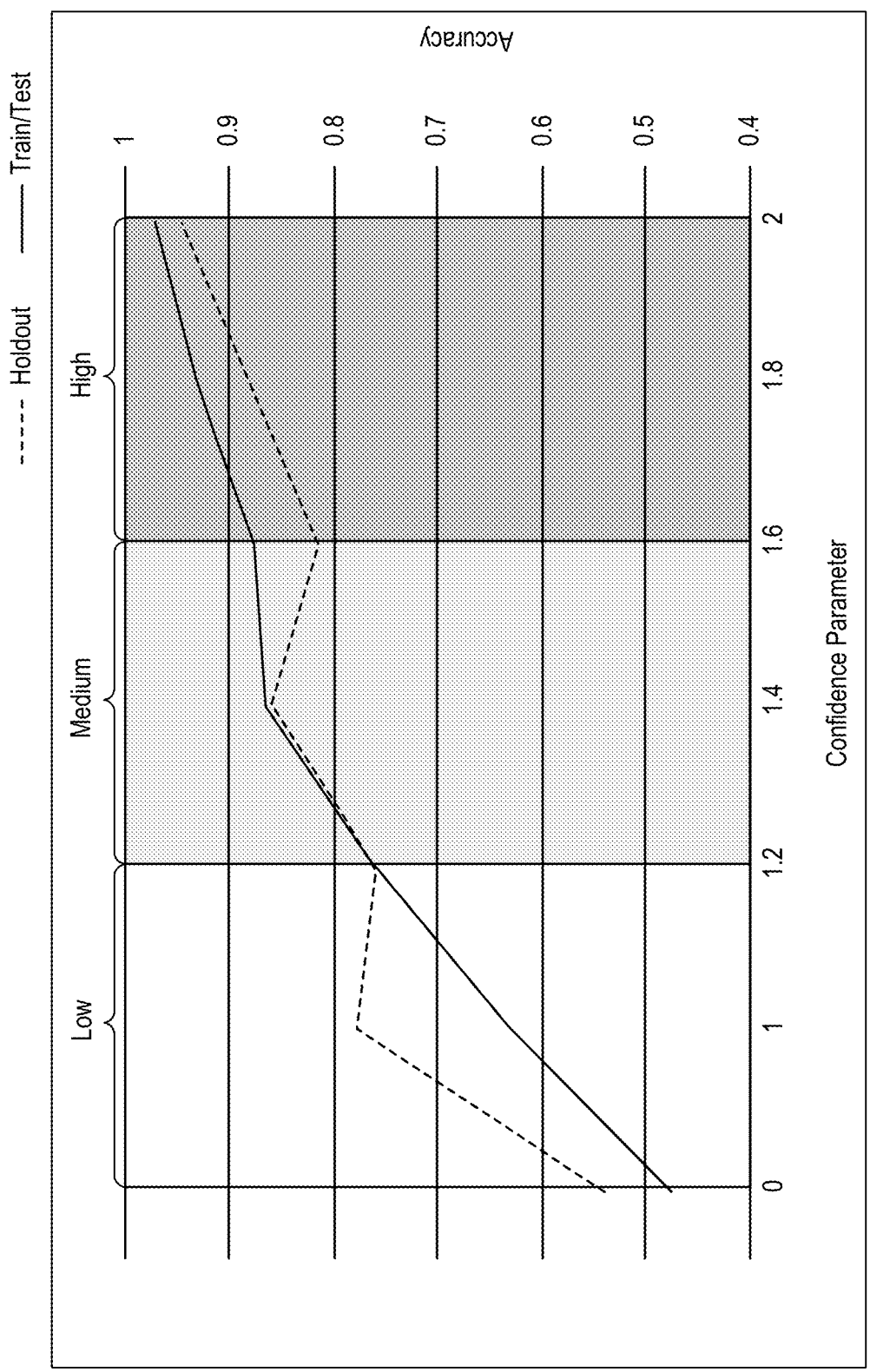

FIG. 6 is a graph plotting Confidence Parameter (CP) against accuracy for CPT assignment. This graph shows the positive correlation between the confidence parameter assigned to each case and the accuracy of the first assigned CPT code. A testing dataset (Train/Test, solid line) and a true holdout dataset (Holdout, dashed line) are plotted. High (CP>=1.6), Medium (1.6>CP>=1.2), Low (1.2>CP) areas are shown, respectively.

Corresponding reference numerals indicate corresponding parts throughout the several views of the drawings.

DETAILED DESCRIPTION

Example embodiments will now be described more fully with reference to the accompanying drawings.

Figure 1:
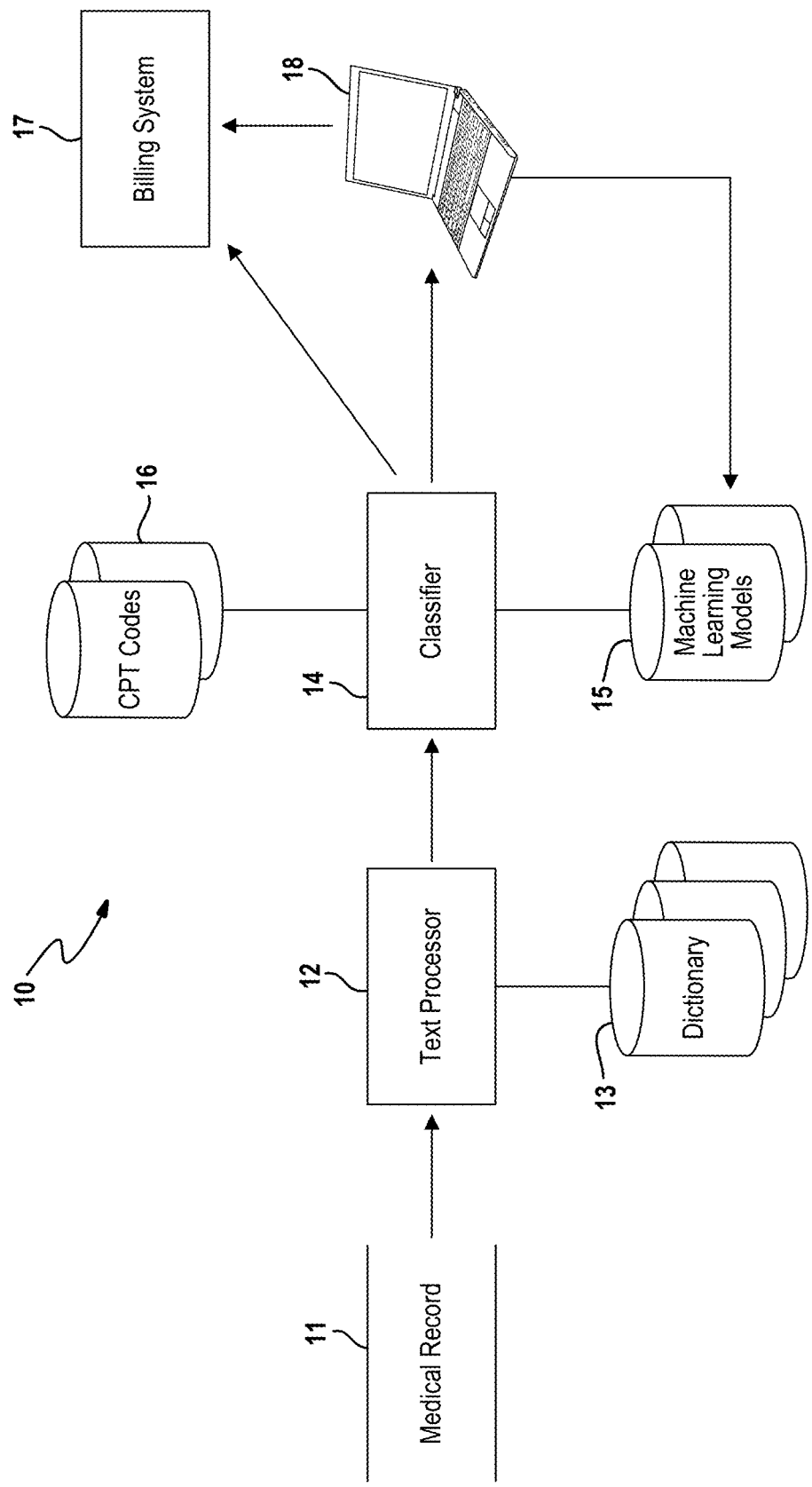
FIG. 1 is a diagram depicting an example embodiment for an automated system for assigning billing codes to medical procedures.

FIG. 1 depicts an example embodiment for an automated system 10 for assigning billing codes for medical procedures. The system 10 is comprised generally of a text processor 12 and a classifier 14. The system 10 may further include one or more dictionaries 13, one or more machine learning models 15 and a listing of possible billing codes 16. Each billing code in the listing of possible billing codes includes a text description of a medical procedure associated with the billing code. While reference is made in this disclosure to Current Procedural Terminology (CPT) codes, it is understood that techniques described herein are applicable to other medical code sets.

The text processor 12 is configured to receive an input record, where the input record represents a medical procedure performed on a patient and the input record includes a text description describing the medical procedure. In the example embodiment, the text processor 12 performs natural language processing on the text description contained in the input record to generate a standardized form suitable for machine learning. Example text processing is further described below.

The classifier 14 receives the input record, including standardized form of the text description, from the text processor 12. The classifier 14 operates to assign a billing code from the listing of possible billing codes 16 to the input record. Briefly, the classifier 14 constructs a feature vector by extracting one or more features from the input record and then, for each billing code in the listing of possible billing codes, computes a classifier score for the feature vector using models constructed from methods such as machine learning. Assignment of the billing code is based on the classifier scores. The classifier 14 can calculate a confidence score for the assigned billing code, where the confidence score quantitates confidence in the assigned billing code. The assignment of a given billing code to the input record can also be based at least in part on the confidence score. Example implementations for the classifier are further described below.

In one embodiment, the input record with an assigned billing code is passed directly to a billing system 17 for processing. In other embodiments, the input record with the assigned billing code are reviewed manually by a billing specialist on a user interface of a computing device 18 before being passed on the billing system 17. The billing specialist may elect to confirm the assignment made by the system or change the assignment made the system. Additionally or alternatively, the results from the system may be used to audit the billing system 17.

In some embodiments, the assignment of the billing code to an input record (either by the system or manually) is used as feedback to improve the machine learning models. That is, the models can be re-trained and/or updated based on the input records with assigned billing codes. Additionally or alternatively, the models can be re-trained and/or updated using feedback from a billing specialist. During a validation process, the billing specialist can indicate whether a billing code assignment was accurate or not and, if not, provide a reason. The feedback from the billing specialist in turn is represented as a vector that is used to re-train the machine leaning models.

Figure 2:
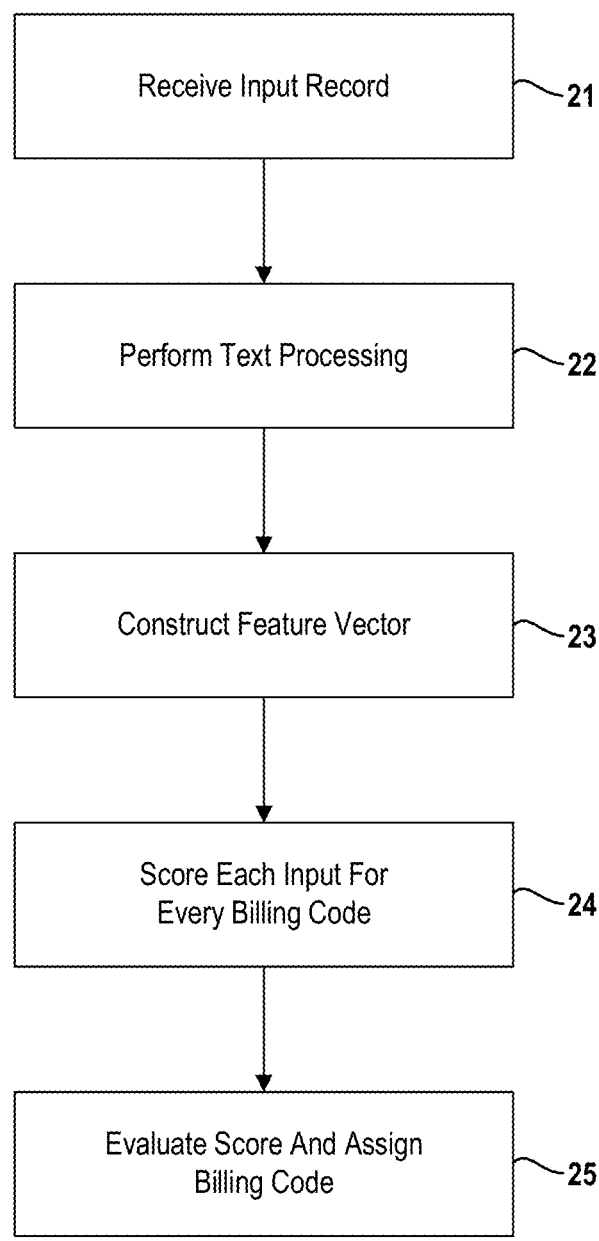
FIG. 2 is a flowchart presenting an overview of an example method for assigning billing codes using machine learning.

FIG. 2 provides an overview of an example method for assigning billing codes for medical procedures. As a starting point, an input record describing a medical procedure is received at 21. The input record includes a text description for the medical procedure. The input record may further include patient characteristics such as patient age, sex, gender, or other identifying information. The input record may include other data attributes regarding the medical procedure, such as procedure duration. These additional attributes may or may not be used in the assignment process.

Natural language and/or text processing is performed at 22 on the input record to generate a standardized form suitable for machine learning. A feature vector is then constructed at 23 from the standardized form of the input record by extracting one or more features from the input record. In one embodiment, each string in the standardized form of the text description is an element in the feature vector. In another embodiment, the feature vector further includes patient age and patient sex as two additional elements of the feature vector. Other constructs for the feature vector are envisioned by this disclosure.

For each billing code in the listing of possible billing codes, the feature vector is scored at 24 using models created using machine learning. Based on the scores, a billing code from the listing of possible billing codes is assigned at 25 to the input record. Additionally, a confidence score can be calculated for the assigned billing code, where the confidence score quantitates confidence in the assigned billing code. The confidence score may be used in the assignment process and/or may be presented to a billing specialist (along with the assigned billing code).

Assuming there a plurality of input records, the method is repeated for each of the input records. That is, a billing code is assigned to each of the input records. It is to be understood that only the relevant steps of the methodology are discussed in relation to FIG. 2, but that other software-implemented instructions may be needed to control and manage the overall operation of the system.

Several natural language processing techniques may be used to process the data into a usable form for machine learning models. An example embodiment for implementing text processing is set forth below. For illustrations purposes, text processing is applied to eight text descriptions which are as follows:

| 1 | CYSTOSCOPY WITH BLADDER FULGURATION/ CLOT EVACUATION |
| 2 | COLONOSCOPY |
| 3 | Colectomy Right Laparoscopic |
| 4 | *L3-4 LAMINECTOMY, DISKECTOMY, BILATERAL* |
| 5 | US guided D&E |
| 6 | trans oral bx\r\nBMA bx\r\n |
| 7 | UTERINE DILITATION AND CURETAGE HYSTEROSCOPY |
| 8 | WAITLIST 292/27/18 CLIPPING OF ANEURYSM |

These example are understood to be illustrative and non-limiting.

To aid in the processing of procedural text and to decrease vocabulary size, the text description from the input record was processed into a standardized form. Because the text description of the medical procedure is typically hand-entered, it is subject to misspellings and frequently contains medical abbreviations and acronyms. First, misspelled words in the text description are corrected. To do so, a dictionary of commonly misspelled words is referenced by the text processor 12, where each entry in this dictionary includes a misspelled word and a corresponding proper spelling for the misspelled word. Upon receiving a text description, each string in the text description is parsed and compared to the entries in the dictionary. If a string in the text description matches a given entry in the dictionary, the string in the text description is replaced with the proper spelling from the dictionary. For example, misspelling of the words discectomy, dilation, and curettage are corrected from the previous text descriptions and resulted as follows (corrections underlined):

| 1 | cystoscopy with bladder fulguration/clot evacuation |
| 2 | colonoscopy |
| 3 | colectomy right laparoscopic |
| 4 | *l3-4 laminectomy, discectomy, bilateral* |
| 5 | us guided d&e |
| 6 | trans oral bx\r\nbma bx\r\n |
| 7 | uterine dilatation and curettage hysteroscopy |
| 8 | waitlist 292/27/18 clipping of aneurysm |

In this example, all of the characters in the strings were also changed to lowercase. Different methods for creating the dictionary of common misspellings are contemplated by this disclosure. In one embodiment, the dictionary underwent hand auditing by a physician or medical professional.

Additionally, common medical abbreviations and acronyms were expanded using domain knowledge. Likewise, a dictionary of abbreviations is referenced by the text processor 12, where each entry in the dictionary includes an abbreviation and expanded text for the abbreviation. Upon receiving a text description, each string in the text description is parsed and compared to the entries in the dictionary. If a string in the text description matches a given entry in the dictionary, the string in the text description is replaced with the expanded text for the abbreviation. With continued reference to examples, d&e was expanded to dilation evacuation in the fifth record and bma was expanded to bone marrow aspiration in the sixth record as seen below (corrections underlined):

| 1 | cystoscopy with bladder fulguration/clot evacuation |
| 2 | colonoscopy |
| 3 | colectomy right laparoscopic |
| 4 | *l3-4 laminectomy, discectomy, bilateral* |
| 5 | us guided dilation evacuation |
| 6 | trans oral bx\r\nbone marrow aspiration bx\r\n |
| 7 | uterine dilatation and curettage hysteroscopy |
| 8 | waitlist 292/27/18 clipping of aneurysm |

Again, different methods for creating the dictionary of abbreviations fall within the scope of this disclosure and the dictionary may undergo hand auditing by a physician or medical professional.

Although these two techniques are particularly effective for assigning billing codes, other text processing was also applied in the example embodiment. For example, punctuation and special characters may be removed from the strings in the text description, including but not limited to the following characters: ! " # $ % & ' ( ) * + , − . / : ; < = > ? @ [ \ ] ^ _ ' {| } ~. Another example is all numbers are removed from the text description, except for five digit numbers. In some cases, five digit CPT billing codes are found in the procedure text and therefore it is helpful to retain these codes during the assignment process.

In yet another example, stop words are removed from the text description. However, in this application, traditional stop words "with" and "without" were shown to improve classification. Although there is not definitive listing of stop words, "with" and "without" are excluded from the listing of stop words in the example embodiment. Application of these additional processing steps are show below:

| 1 | cystoscopy with bladder fulguration clot evacuation |
| 2 | colonoscopy |
| 3 | colectomy laparoscopic |
| 4 | l laminectomy discectomy bilateral |
| 5 | us guided dilation evacuation |
| 6 | trans oral bx\r\nbone marrow aspiration bx\r\n |
| 7 | uterine dilatation curettage hysteroscopy |
| 8 | waitlist clipping aneurysm |

Finally, common endings have been removed or truncated from each string and excess white spaces have been removed from each text description. In this example, common endings may include -ing as well as medically more common endings, such as -omy or -tion. These common endings are merely illustrative and non-limiting. Unigrams (single word features) are formed from the strings remaining in the text description as seen below (each unigram separated by a /):

| | |
|---|---|
| 1 | cystoscopi/with/bladder/fulgur/clot/evacu |
| 2 | colonoscopi |
| 3 | colectomi/laparoscop |
| 4 | laminectomi/discectomi/bilater |
| 5 | guid/dilat/evacu |
| 6 | trans/oral/bx/bone/marrow/aspir |
| 7 | uterin/dilat/curettag/hysteroscopi |
| 8 | waitlist/clip/aneurysm |

Alternatively, or additionally, bigrams (features as word pairs) can be formed from the strings remaining in the text description as seen below (each bigram separated by a /):

| | |
|---|---|
| 1 | cystoscopi with/with bladder/bladder fulgur/fulgur clot/clot evacu |
| 2 | colonoscopi |
| 3 | colectomi laparoscop |
| 4 | laminectomi/discectomi/discectomi bilater |
| 5 | guid dilat/dilat evacu |
| 6 | trans oral/oral bx/bx bone/bone marrow/marrow aspir |
| 7 | uterin dilat/dilat curettag/curettag hysteroscopi |
| 8 | waitlist clip/clip aneurysm |

Formation of skip-grams and other n-grams are also contemplated as well as correlations (i.e., pairs of words that are contained in a procedure text but not necessarily immediately adjacent to one another).

Word embedding may be applied to the text description of the input records received from the text processor 12 and used as input to the classifier 14. For instance, term frequency-inverse document frequency (TfIDF) matrixes may be created from the standardized form of the text descriptions. Each word in the TfIDF matrix has a numerical value representing the importance of the word to the text. In one example, the TfIDF matrix may include both unigrams and bigrams and may include the entire vocabulary or a subset based on a selected parameter such as the likelihood ratio. In this example, terms in which document frequency is more than 0.9 were removed from the TfIDF matrix, as these terms were common and likely do not contain quality information to aid in classification. A sparse TFIDF matrix is obtained by applying these filters. Categorical features (such as sex) and continuous numerical features (such as age) from the input records can be joined with TFIDF matrix to expand the matrix. This type of sparse matrix is particularly suitable as an input to support vector machines (SVM) and random forest (RF).

In another instance of word embedding, word2vec representation of the text descriptions from the input records is used as a method to maintain more context. Due to its sparsity, some machine learning algorithms do not work well with the TfIDF method and the word2vec model can incorporate more of the text into a translated form. Word2vec represents each word in low dimensional continuous vector space, where similar words are mapped to nearby points. These word vectors, trained on large corpus, can then be used in classification. In one example, for more relevant word2vec training and potentially better results, one can use pre-trained word2vec embeddings from biomedical text. Each word in this model is represented as 200 dimensional vector. Since most descriptions contain multiple words, the result is a word matrix for each procedure. The word2vec method of text transformation is preferred for Extreme Gradient Boosting and deep neural network classification algorithms. Other types of word embedding techniques also fall within the broader aspects of this disclosure.

Following text processing, billing codes are classified by the classifier 14 using machine learning. In one example embodiment, the billing codes are classified using a deep neural network, such as Label-Embedding Attentive models (LEAM). Briefly, a distinctive feature of using the LEAM model is that procedure text descriptions were encoded using the word2vec embedding. In traditional deep learning models for text classification, only words within the text are embedded. By a learnable function, a text sequence representation is derived by mapping embedded words into a latent space. In this example embodiment, LEAM brings in additional information by embedding not only the words in the text but also the target labels from the listing of possible billing codes (i.e., the formal description for each Anesthesia CPT code). Each word from this description is embedded and the average is taken as the embedding of the label. Next, LEAM computes a "compatibility matrix" between embedded words and labels via cosine similarity. LEAM used convolution on the "compatibility matrix" and learned to calculate the attention score for each word. A text sequence representation was then derived as the average of embedded words, weighted by the attention scores. In one example, the model is implemented using the Tensorflow machine learning framework.

While reference is made throughout this application to a particular deep learning model (i.e., LEAM), Long Short Term Memory networks and other types of deep learning models are also contemplated by this disclosure. Moreover, the assignment techniques are not limited to deep learning. Other types of machine learning methods fall within the scope of this disclosure, including but not limited to Support Vector Machines, Random Forest, and Extreme Gradient Boosting.

Term frequency-inverse document frequency (Tf-IDF) itself can also be used to score each of the billing codes in the listing of possible billing codes. That is, for each billing code in the listing of possible billing codes, a term frequency-inverse document frequency (Tf-IDF) score is computed for the input text description in relation to the text description for a given billing code in the listing of possible billing codes, where the Tf-IDF score for the given billing code is a summation of each score for each string in the input text description. Other features from the input record can be incorporated into the Tf-IDF score. For example, age and/or sex can be made into a text string and appended onto the text description. In another example, age and/or sex can be made into categorical variables (e.g., to distinguish infants, a particular value is assigned to persons with an age less than one). Again, age and sex are merely non-limiting examples of features that can be used to determine the Tf-IDF score. Additionally, there are many possible calculations for determining Tf-IDF scores and the implementation as described here is not limited to any one calculation. In sum, Tf-IDF is contemplated for use in creating a document-term matrix as input for a machine learning algorithm and/or used independently to score billing codes.

To assign a billing code, the Tf-IDF scores for all of the billing codes are ordered from highest to lowest. In one example, the billing code with the highest Tf-IDF score is assigned to the input record. In another example, a confidence parameter is computed and used to determine the assignment of the billing code. The confidence parameter is computed as a ratio of the highest score to the second highest score. If the value of the confidence parameter is high (e.g., >1.6), then the billing code with the highest Tf-IDF score is assigned to the input record; otherwise (i.e., <1.6), no billing code is assigned to the input record. In such cases, the highest n scores are presented to a billing specialist (along with a confidence for assignment) who in turn manually assigns a billing code of the input record. Other methods for computing a confidence parameter are contemplated by this disclosure.

Figure 3:
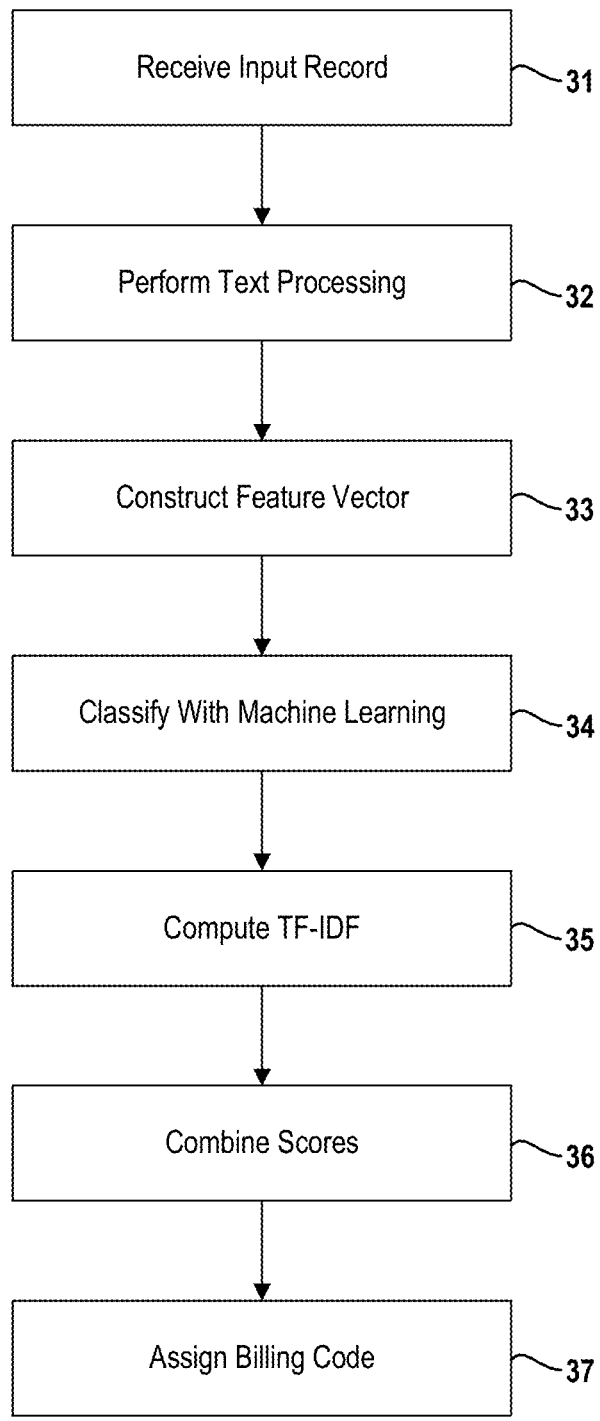
FIG. 3 is a flowchart depicting an example embodiment for assigning billing code using an ensemble method in accordance with this disclosure.

FIG. 3 illustrates an example embodiment in which Tf-IDF scoring is combined with a machine learning technique to assign billing codes as part of an ensemble system. One or more input records each describing a medical procedure is received at 31 for classification. In this example embodiment, the input record includes at least patient age, patient sex and a text description for the medical procedure.

To generate a standardized form suitable for machine learning, text processing is performed on the input record at 32, for example in the manner described above. In some embodiments, classification of input records could occur without text processing. In any case, a feature vector is constructed at 33 by extracting one or more features from the input record. In this example embodiment, elements in the feature vector include each string in the text description, along with a text string for the age and a text string for the sex of the patient.

In this example embodiment, each billing code in the listing of possible billing codes is first classified at 34 using a label-embedding attentive model (LEAM). For a given feature vector, LEAM computes a probability or percentage of confidence score for each billing code in the listing of possible billing codes. The billing codes are then ordered highest to lowest based on the corresponding confidence score. To assist with the assignment process, a confidence parameter is also derived from the confidence scores. In the example embodiment, the confidence parameter is ratio of the highest confidence score to the second highest confidence score. For example, confidence parameter of three is computed when the highest confidence score is 75% and the second highest confidence score is 25%.

Next, each billing code in the listing of possible billing codes is scored at 35 using Tf-IDF. In this example, for every unigram and bigram associated with an input record, Tf-IDF assigns a score to each feature for each possible billing code. Within each possible billing code, the feature scores are summed to generate a Tf-IDF score for each possible billing code. The billing code are ordered from highest to lowest based on the corresponding Tf-IDF scores. Likewise, a confidence parameter is computed to assist with billing code assignment. In this case, the confidence parameter is also ratio of the highest confidence score to the second highest confidence score. For example, a confidence parameter of two is computed when the highest billing code Tf-IDF score is 28 and the second highest billing code confidence score is 14.

From these scores, a composite score is determined at 36 by combining the classifier score with the Tf-IDF score for each possible billing code. In an example embodiment, the ordered classifier scores are assigned a rank from 1 to n starting with the highest score. That is, the highest classifier score is assigned a value of one, the second highest classifier score is assigned a value of two, the third highest classifier score is assigned a value of three, and so forth. An abbreviated example is set forth below:

| Rank | CPT | LEAM Probability |
|---|---|---|
| 1 | 00910 | 0.94757 |
| 2 | 00912 | 0.01311 |
| 3 | 00914 | 0.01149 |

Tf-IDF scores are also assigned a rank value in a similar way.

| Rank | CPT | Tf-IDF |
|---|---|---|
| 1 | 00912 | 150.64 |
| 2 | 00914 | 117.59 |
| 3 | 00910 | 83.79 |

The composite score of a given billing code is then determined by summing the rank assigned to the given billing code by the two methods as seen in the following example.

| CPT | composite score |
|---|---|
| 00912 | 3 |
| 00910 | 4 |
| 00914 | 4 |

A composite of the confidence parameter is also performed by combining the High/Medium/Low outputs between the methods in the ensemble. For example, if both the LEAM and Tf-IDF components have the same top predicted CPT but the LEAM model produces a medium confidence and the Tf-IDF a high, the ensemble will return a High-Medium confidence for the case in question. If there are different top choices the confidence will return as low. Other methods for combining scores also fall within the broader aspects of this disclosure.

Lastly, a billing code from the listing of possible billing codes is assigned at 37 to the input record based on the composite scores for each of the billing codes in the listing. In one embodiment, the billing code with the lowest composite score is assigned automatically to the input record and the input record is in turn forwarded on to a billing system. Continuing with the example above, the billing code 00912 is assigned to the input record. In another embodiment, the billing code with the lowest composite score is assigned automatically only if it was the lowest ranked by each of the scoring methods; otherwise, the billing code scoring is presented to a billing specialist for manual review and assignment.

In yet another embodiment, the billing code with the lowest composite is always presented to a billing specialist for confirmation before being sent on to the billing system. In addition to the assigned billing code, the top n billing codes for a given input record may be presented to the billing specialist (along with the input record), where the top n billing codes have lowest composite scores from amongst the billing codes in the listing of possible billing codes.

To assist the billing specialist, a confidence parameter or label may also be presented. Again, the confidence parameter for LEAM is the ratio of the highest confidence score to the second highest confidence score. For a more intuitive output, the confidence parameter can be translated to a confidence label, such as "high confidence", "medium confidence" or "low confidence". In one example, ratios having a value greater than twenty (20) are deemed high confidence, ratios with a value in between twenty and ten are deemed medium confidence and ratios with a value lower than ten are deemed low confidence. Cutoff values are derived empirically and may be varied depending upon the desired system accuracy.

Similarly, the confidence parameter for Tf-IDF can be translated to a confidence label. In this case, ratios having a value greater than 1.6 are deemed high confidence, ratios with a value in between 1.6 and 1.2 are deemed medium confidence, and ratios with a value lower than 1.2 are deemed low confidence. Cutoff values are derived empirically and may be varied depending upon the desired system accuracy.

In some embodiments, the confidence labels from the two scoring methods are consolidated. For instance, if the top billing code is the same between methods and the confidence label for both methods are same (e.g., high), then this confidence label is presented to the billing specialist as the confidence label for the assigned ensemble billing code. On the other hand, if the top billing codes or the confidence labels differ between the two scoring methods, then a confidence label is assigned in accordance to a rule. For example, the consolidated confidence label may be set to an average of the two confidence labels (i.e., high/medium medium or high/low medium) or set to the lowest of the two confidence labels. If top billing codes differ between methods a "low" or "disagreement" confidence can be returned. In this way, billing codes and confidences are assigned.

As proof of concept, data records were gathered for all patients undergoing elective or urgent procedures with an assigned valid anesthesiology CPT code and an operative date between Jan. 1, 2014 and Dec. 31, 2016 using the Multicenter Perioperative Group (MPOG) registry. Individual institutions which contributed to this dataset ranged from large academic hospital groups to smaller community based practices. A second dataset was created for external validation and generalization of the models created in this study. This second dataset was created using data from a single institution that was not included in the previous dataset. In this disclosure, the larger multi-institution data set is referred to as "Train/Test" dataset and second single institution dataset is referred to as the "Holdout" dataset. For the Holdout dataset, patients undergoing elective or urgent procedures with an assigned valid anesthesiology CPT code and an operative date between Oct. 1, 2015 and Nov. 1, 2016 were selected. Only sites which submitted valid data types were eligible for inclusion.

To maximize the number of cases included in the study, minimal information was used for modeling, and included only features found across all anesthesia records, such as: patient age, patient sex, American Society of Anesthesiologists physical status (ASA), emergent status, procedure text, procedure text length (number of words in procedure text), and procedure duration. This information is similar but more limited to the information available to a medical biller when making CPT assignment. Institutional assigned anesthesia CPTs were used as labels for each case and each case represents an instance for machine learning modeling. The primary outcome is CPT assignment accuracy, defined per anesthetic case as a correct first choice CPT. Continuous features underwent scaling through normalization to achieve properties of a standard normal distribution with a mean of zero and a standard deviation of one.

To ensure validity of the original CPT codes, 501 random cases selected from the Train/Test dataset were hand audited by an anesthesiologist. Blinded to the original assigned CPT, the anesthesiologist determined the primary CPT code for each of the 501 assigned cases. These anesthesiologist-assigned CPTs were then compared to the CPT codes assigned from the institutions which exist in the MPOG database. This was used as an assessment of validity of the labels used within this study.

Finally, to determine the generalized ability of the models in predicting anesthesia CPT, each model was tested on data from the Holdout dataset.

Data is presented as frequencies with percentages or means with standard deviation, as appropriate. Computed differences between groups using Chi-Squared test for categorical features, student's t-test for continuous. We defined a clinically significant difference in proportion between CPT groups to be 5.0%.

Key metrics of the datasets used in this study can be found in Table 1 below:

| Category | | Train/Test | Holdout | P-Value |
|---|---|---|---|---|
| Case Demographics | | | | |
| Unique Anesthesia Cases | | 1,164,343 | 58,510 | |
| Unique Anesthesia CPTs | | 262 | 232 | |
| CPT Categories | | | | |
| Head | 00100-00222 | 156017 (13.4%) | 14934 (25.5%) | <0.0001 |
| Neck | 00300-00352 | 53302 (4.6%) | 3238 (5.5%) | <0.0001 |
| Thorax (chest, shoulder) | 00400-00474 | 58001 (5.0%) | 2746 (4.7%) | 0.0061 |
| Intrathoracic | 00500-00580 | 57908 (5.0%) | 3778 (6.5%) | <0.0001 |
| Spine and Spinal Cord | 00600-00670 | 36520 (3.1%) | 1291 (2.2%) | <0.0001 |
| Upper Abdomen | 00700-00797 | 170005 (14.6%) | 7646 (13.1%) | <0.0001 |
| Lower Abdomen | 00800-00882 | 227202 (19.5%) | 7658 (13.1%) | <0.0001 |
| Perineum | 00902-00952 | 105208 (9.0%) | 3584 (6.1%) | <0.0001 |
| Pelvis (except hip) | 01112-01190 | 4904 (0.4%) | 227 (0.4%) | 0.9999 |
| Upper Leg (except knee) | 01200-01274 | 35094 (3.0%) | 1162 (2.0%) | <0.0001 |

-continued

| Category | | Train/Test | Holdout | P-Value |
|---|---|---|---|---|
| Knee and Popliteal Area | 01320-01444 | 45967 (3.9%) | 1502 (2.6%) | <0.0001 |
| Lower Leg (below knee) | 01462-01522 | 37350 (3.2%) | 1217 (2.1%) | <0.0001 |
| Shoulder and Axilla | 01610-01682 | 24076 (2.1%) | 907 (1.6%) | <0.0001 |
| Upper Arm and Elbow | 01710-01782 | 7110 (0.6%) | 408 (0.7%) | 0.0129 |
| Forearm, Wrist and Hand | 01810-01860 | 38149 (3.3%) | 1269 (2.2%) | <0.0001 |
| Radiological Procedure | 01916-01936 | 45378 (3.9%) | 3329 (5.7%) | <0.0001 |
| Burn Debridement | 01951-01953 | 1054 (0.1%) | 1 (0.0%) | <0.0001 |
| Obstetric | 01958-01969 | 61098 (5.2%) | 3516 (6.0%) | <0.0001 |
| Other Procedure | 01990-01999 | 0 (0.0%) | 97 (0.2%) | N/A |
| Patient Demographics | | | | |
| Female | | 659272 (56.6%) | 32078 (54.8%) | <0.0001 |
| Age | | 50.5 (21.7) | 49.9 (23.1) | |
| ASA 1 | | 111269 (9.6%) | 6307 (10.8%) | <0.0001 |
| ASA 2 | | 536752 (46.5%) | 25998 (44.4%) | <0.0001 |
| ASA 3 | | 428397 (37.1%) | 23095 (39.5%) | <0.0001 |
| ASA 4 | | 75230 (6.5%) | 2969 (5.1%) | <0.0001 |
| ASA 5 | | 1600 (0.1%) | 132 (0.2%) | <0.0001 |
| ASA 6 | | 16 (0.0%) | 9 (0.0%) | <0.0001 |
| Emergent | | 52367 (4.5%) | 2385 (4.1%) | <0.0001 |

The Train/Test data was comprised of 1,164,343 unique cases across 16 institutions and spanning 262 unique anesthesia CPT codes. The Holdout dataset was comprised of 58,510 unique cases across a single institution and spanning 232 unique anesthesia CPT codes. The Train/Test dataset included 227 of the 232 codes contained in the Holdout dataset. The five anesthesia CPT codes unique to the Holdout dataset were: 01180, 01990, 01991, 01192, and 01999. Fifty-seven percent of patients were female. The mean age was 50.5 years old (55.0 median). The ASA distribution was primarily ASA 2 and ASA 3, and 4.5% of cases were listed as emergent status. CPT code ranges can be defined by body area classification. When grouped using these body area classifications, the CPT codes were unevenly distributed within the datasets. Contributions of cases into each CPT grouping varied greatly between individual institutions, but the distribution reflects the contents of the overall MPOG database. The Holdout dataset was clinically similar (<=5.0% difference in frequency) to the Train/Test dataset. As the group sizes are large, they each showing statistical significance but the majority do not show clinical significance. The two CPT categories that do show clinical significance are "Head" and "Lower Abdomen" (Head: 13.4% Train/Test vs. 25.5% Holdout; Lower Abdomen: 19.5% Train/Test vs. 13.1% Holdout). There were two additional body areas where there was an overwhelming relative sparsity in the dataset: Burn Debridement (1054 cases vs 1 between the Train/Test and the Holdout datasets, respectively) and Other Procedure (0 cases represented in the Train/Test vs 97 in the Holdout data).

In the Test/Train dataset, 36,356 cases were identified as missing procedure text, representing 0.1% of the data. The Holdout dataset had 17 such cases (0.0% of the data). 8353 unique medical misspellings were identified. The top misspelled words by frequency were physician hand audited for validity and placed into a dictionary which was used in the text processing prior to ML modeling. The top misspelled medical terms included "discectomy", "dilatation", "curettage", and "excision", along with longer terms like "esophagogastroduodenoscopy" and "cholangiopancreatography". In all, 21.3% of all cases contained at least one word that was misspelled and subsequently corrected.

Procedure text was the most important variable in assigning anesthesia CPT codes. Procedure text was sparse for most cases with an average word count of approximately 10 words per case. The vocabulary size across all cases was 25098 unique words. Most individual words were rare, occurring in less than 10 cases across both datasets, accounting for 19159 or 76.3% of the vocabulary size. Models assign weight to the features. The higher the weight the more important the feature. In the SVM model, the average weight assigned to each feature for CPT prediction was 7.9 for individual words; whereas, the average combined weight of all words was 337.5 for each CPT. Weights for all other features was considerably lower than the combined weight: Text Length (4.3), Sex (2.1), Emergent Status (1.5), ASA (6.1), Case Duration (1.5), and Age (3.2).

In total, five distinct supervised machine learning classification models (RF, LSTM, XGBoost, SVM, and LEAM) were implemented. In the Test/Train dataset, Random Forest modeling yielded an overall average accuracy of correct CPT assignment of 82.0% (±7.1%). Using body area classifications, the class accuracy ranged from a low of 70.7% to a high of 92.0%. SVM (87.9%±0.1%), XGBoost (87.9%±0.2%), and LSTM (86.4%±1.5%) were all more accurate than the RF model. As there was wide variability in CPT frequency in the dataset CPT weighting was implemented in an attempt to boost the accuracy of the low performing CPTs. Weighting improved individual CPT accuracy but lowered overall accuracy. The LEAM model yielded an overall accuracy of 85.9%.

Figure 4:
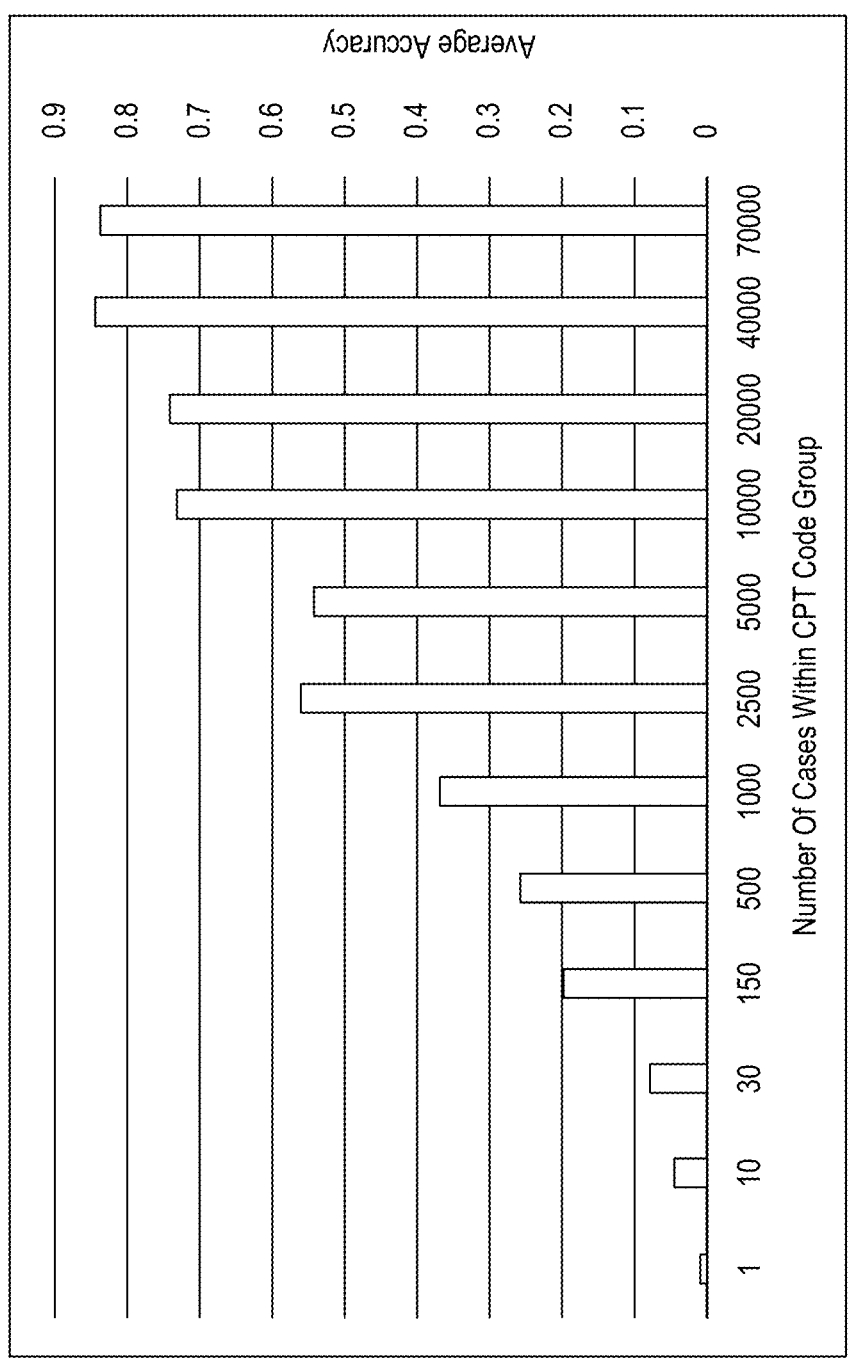
FIG. 4 is a graph showing correlation between number of cases per CPT code and model accuracy using a support-vector machine (SVM) machine learning model. The number of cases in the CPT group is plotted on the x-axis (ex. "150" shows the accuracy for the CPT codes in which the number of cases for each CPT is between 150 and 500); whereas, the average accuracy of CPT group is shown on the y-axis.

There was a general positive correlation between the number of cases in a specific CPT and the accuracy of the models for that specific CPT as seen in FIG. 4. CPTs with a higher number of cases in the Train/Test dataset tend to be more accurate than those with lower case numbers. In an attempt to increase the accuracy of the model for CPTs with a low number of cases, weighting techniques were applied. Weighting of low frequency CPTs improved individual CPT accuracy, but decreased overall model accuracy.

In analyzing specific CPTs with low accuracy, generalized case ambiguity (multiple CPTs used to label the similar cases) was often a major concern. More specifically, there were CPT combinations that were often assigned interchangeably both between institutions and even within the same institution. FIG. 5 shows a heat map for the LSTM model as a modified confusion matrix for the Pelvis (no hip) CPT body categorization. This figure illustrates the association between the model's selections and the institutional assignment. The 6 CPTs represented in this body categorization expand into 23 separate CPT assignments by the model. The heat map shows ambiguity in model assignment as illustrated by CPT 01160 (closed procedures involving symphysis pubis or sacroiliac joint) preferentially labeling 01170 (open procedures involving symphysis pubis or sacroiliac joint). The remaining CPT codes in this illustration are more accurate, especially 01112 and 01130.

From the SVM model, a confidence parameter (CP) was created from comparing the top 3 results for each case. The top three primary anesthesia CPT codes for each case were output in order of decreasing confidence. To aid in prediction accuracy, we grouped the case predictions by CP and found a direct positive correlation between the CP correct assignment of the first CPT as determined by the model (FIG. 6). When the confidence parameter is divided into three large groups: "High" (CP>=1.6), "Medium" (1.6>CP>=1.2), and "Low" (1.2>CP) categories, the "High" category returns a 95.2% accuracy and represents 54.8% of the Train/Test dataset. When selecting more stringent criteria (CP>=2.0) first CPT accuracy increases to 97.1% and the coverage falls to 39.3% of the data. Accuracy within the top 3 (defined as the correct CPT found at any of the top 3 predication CPTs from the model) was 99.1% (CP>=1.6) and 98.6% (CP>=2.0) for the Train/Test dataset.

The best performing machine learning model by overall accuracy in the Holdout dataset was the SVM model (81.2%). When stratifying by the same "High", "Medium", and "Low" CP metrics, one finds a 93.1% accuracy for the "High" (CP>=1.6) group encompassing 58.0% of the dataset. At the more stringent confidence (CP>=2.0), accuracy again increases (94.7%) with a decrease in dataset coverage to 48.0%. Accuracy within the top 3 was 97.0% (CP>=1.6) and 96.3% (CP>=2.0) for the Holdout dataset. If the Train/Test and Holdout dataset were merged and a random 58,510 cases were held out, the overall accuracy increases to 84.5%, 94.0% for "High", and 95.3% for the more stringent levels, covering 62.0% and 49.4% of cases, respectively.

The overall accuracy of LEAM was 82.1% for the Holdout dataset. Applying the CP to LEAM, the accuracy is improved to 95.0% accuracy for the "High" (CP>=1.6) group encompassing 62.0% of the dataset. At the more stringent confidence (CP>=2.0), accuracy increases (96.9%) with a dataset coverage to 48.3%. Accuracy within the top 3 was 98.4% (CP>=1.6) and 98.7% (CP>=2.0) for the Holdout dataset.

Institution assigned primary anesthesiology CPTs were used as the gold-standard labels developing the models. To assess for potential error with the gold-standard, a physician hand validation was conducted over 501 cases from the Train/Test dataset. In this process, 25 of 501 (5.0%) cases were found to be misclassified by primary anesthesia CPT when analyzed by physician hand auditing was compared to institution input CPT within the database. Nine of these cases were correctly identified by the SVM model.

This disclosure presented highly predictive models to correctly and automatically assign anesthesiology CPT billing codes from common perioperative EMR data. Several supervised machine learning methods were tested and SVM was found to yield to yield the best overall accuracy (87.9% Train/Test). The LEAM model's overall accuracy was 85.9%. By creating a confidence parameter, one is able to stratify cases into predictive groups increasing SVM accuracy to 95.2% (54.8% of the cases) and 97.1% (39.3% of cases), which is above the 5% threshold set for this study. The strong positive correlation between the CP and accuracy allows for titration of the system to a desired level of accuracy and is most feasible in its current form for rapid implementation in anesthesia CPT assignment.

In testing models on the Holdout dataset (data from an institution that was not included in the Train/Test dataset), one is able to show the generalizability of the models. The SVM model yielded an overall 81.2% accuracy for this dataset, and while applying the CP, SVM showed an accuracy of 93.1% (58.0% of cases) and 94.7% (48.0% of cases). The Label-Embedding Attentive Model (LEAM) was chosen based on its ability to weight relevant words within a text sequence. While SVM model performed as well as the LEAM for the Train/Test dataset, LEAM outperformed SVM in the Holdout dataset: 95.0% (62.0% of cases) and 96.9% (48.3% of cases). This is expected as the LEAM model embeds labels, containing more information in their assignments, and thus capable of better assessment of untrained data. These models were implemented at MPOG to expedite research and quality projects. CPT assignment is now attained upon upload of clinical medical records greatly reducing the lag in receiving anesthesia billing data.

Speed of processing was a significant. The model was able to process over 1 million cases in under 10 min as a web application. The primary utility of these models exists in directly aiding anesthesiology CPT assignment. Both the SVM and LEAM can automatically assign CPTs with high accuracy. In leveraging the confidence parameter, one can reliably automate the assignment of CPT billing codes in higher confidence cases while redirecting administrative efforts on cases with lower confidence. Within this disclosure it was estimated decreasing assignment workload by 40-60%. A previous reported error rate in anesthesia CPT assignment was found to be 38% and our own case physician review found a 5% rate of misclassification of CPT codes. Both are above the level of error for the higher confidence results (4.8% and 2.9% respectively). Furthermore, these models could be used to narrow the assignment choices for medical billing specialists. If one looks at the top 3 choices from the SVM model, top 3 accuracy of is 99.1% (CP>=1.6) and 98.6% (CP>=2.0). The LEAM accuracies are similar. This model could aid coding personnel by providing a smaller subset of CPT choices for assignment. This suggests the tool may be useful in auditing to find discrepancies when compared to manual assignments which could help identify potential errors in coding. Quality assurance and research projects which use CPT information would also benefit from use of these models.

The billing assignment process is a time-consuming effort which consists of more than CPT code assignment. Billing departments and vendors also spend a considerable amount of time processing information for reimbursement, as documentation errors are common (26). Within our datasets we found medical misspellings accounted for 33.3% of the total vocabulary, and 21.3% of cases contained at least one misspelled term. As misspelled terminology likely complicates CPT assignment, natural language processing of the procedure text is a useful tool even without downstream machine learning applications.

One study estimated that 15.7% of anesthesia cases contain at least one documentation error after the first billing attempt and the median time to correct documentation errors was 33 days. An estimated 1.3% of all anesthetic cases went without reimbursement due to improper documentation and failure to correct errors. Charge lag, as defined as the number of days between procedural date of service and date of transmission to payer, was between 5 and 17 days in one single-center study. Hospital cost and reimbursement are directly tied to this turnover, and with billing data increasingly used both in research and quality improvement initiatives (QI), rapid and accurate characterization is even more important.

The assignment technique set forth above is able to process over 1 million cases in under 10 minutes as a web application. Any amount of time saved in processing can result in significant monetary impact. One study found that an estimated 3.0% of total annual receipts from anesthesiology practices can be gained by decreasing the average charge lag by 7.3 days (10). With hospital operating margins between 2-3% this represents a significant savings opportunity without compromising patient care (27-29). A CPT prediction tool can be used to refocus resources away from CPT assignment and towards areas such as documentation errors to further improve the overall process.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware, or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for assigning billing codes for medical procedures, comprising:
   receiving, by a computer processor, a listing of possible billing codes, each billing code in the listing of possible billing codes includes a text description of a medical procedure associated with the billing code;
   receiving, by the computer processor, an input record describing a medical procedure, where the input record includes an input text description for the medical procedure and the input text description is comprised of one or more strings;
   receiving, by the computer processor, a first dictionary of common misspellings, each entry in the first dictionary includes a misspelled word and a corresponding proper spelling of the misspelled word;
   for each string in the input text description, comparing, by the computer processor, the string to entries in the first dictionary and, in response to the string matching a given entry in the first dictionary, replacing the string in the input text description with proper spelling;
   receiving, by the computer processor, a second dictionary of abbreviations, each entry in the second dictionary includes an abbreviation and expanded text for the abbreviation;

for each string in the input text description, comparing, by the computer processor, the string to entries in the second dictionary and, in response to the string matching a given entry in the second dictionary, replacing the string in the input text description with expanded text for the abbreviation;

constructing, by the computer processor, a feature vector by extracting one or more features from the input record, where the input text description serves as a feature in the feature vector;

for each billing code in the listing of possible billing codes, computing, by the computer processor, a classifier score for a given billing code in relation to the feature vector using machine learning;

for each billing code in the listing of possible billing codes, computing a term frequency-inverse document frequency (Tf-IDF) score for each of the one or more strings of the input text description in relation to the text description for a given billing code in the listing of possible billing codes, where the Tf-IDF score for the given billing code is a summation of each score for each string in the input text description;

for each billing code in the listing of possible billing codes, combining the Tf-IDF score with the classifier score to form a composite score; and assigning a billing code to the input record from the listing of possible billing codes based on the composite scores for each of the billing codes in the listing of possible billing codes.

2. The method of claim 1 further comprises performing natural language processing on the input text description prior to constructing a feature vector.

3. The method of claim 1 wherein the input record further includes age of patient and sex of patient, such that the age of the patient is a second feature in the feature vector and the sex of the patient is a third feature in the feature vector.

4. The method of claim 1 further comprises calculating a confidence score for the assigned billing code, where the confidence score quantitates confidence in the assigned billing code and the billing code is assigned to the input record based in part on the confidence score.

5. The method of claim 4 wherein the confidence score is calculated as a ratio of the classifier score with highest value to the classifier score with second highest value.

6. The method of claim 1 further comprises updating models used in the machine learning based on the billing code assigned to the input record.

7. The method of claim 1 further comprises presenting top n billing codes for the input record, where the top n billing codes have highest classifier scores from amongst the billing codes in the listing of possible billing codes.

* * * * *